(12) United States Patent
Bower et al.

(10) Patent No.: US 11,837,367 B1
(45) Date of Patent: Dec. 5, 2023

(54) COMPUTING SYSTEM CONFIGURED FOR AGGREGATING AND DISPLAYING DATA

(71) Applicant: Allscripts Software, LLC, Raleigh, NC (US)

(72) Inventors: Scott Bower, Raleigh, NC (US); David Windell, Raleigh, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 1187 days.

(21) Appl. No.: 15/215,270

(22) Filed: Jul. 20, 2016

(51) Int. Cl.
| | | |
|---|---|---|
| *G16H 80/00* | (2018.01) | |
| *G16H 40/63* | (2018.01) | |
| *G16H 50/20* | (2018.01) | |
| *G16H 10/60* | (2018.01) | |
| *G16H 20/10* | (2018.01) | |

(52) U.S. Cl.
CPC .............. *G16H 80/00* (2018.01); *G16H 10/60* (2018.01); *G16H 20/10* (2018.01); *G16H 40/63* (2018.01); *G16H 50/20* (2018.01)

(58) Field of Classification Search
CPC ........ G06Q 50/22; G06Q 50/24; G06F 19/30; G06F 19/32; G06F 19/325; G06F 19/34; G06F 19/3418; G06F 19/36; G16H 10/00; G16H 10/60; G16H 20/00; G16H 40/00; G16H 40/20; G16H 80/00
USPC ......................................................... 705/2, 3
See application file for complete search history.

(56) References Cited

U.S. PATENT DOCUMENTS

| | | |
|---|---|---|
| 8,015,034 B2 | 9/2011 | Zhou et al. |
| 8,060,377 B2 | 11/2011 | Dunham et al. |
| 2011/0161110 A1* | 6/2011 | Mault ..................... G16H 40/67 705/3 |
| 2011/0246220 A1* | 10/2011 | Albert .................... G06Q 10/00 705/2 |
| 2012/0221352 A1 | 8/2012 | Georgeff |
| 2012/0290322 A1* | 11/2012 | Bergman ............... G06Q 50/24 705/3 |
| 2013/0110537 A1* | 5/2013 | Smith .................... G06Q 10/06 705/2 |
| 2013/0179178 A1 | 7/2013 | Vemireddy et al. |
| 2015/0051917 A1 | 2/2015 | Nikolova-Simons et al. |
| 2015/0051922 A1* | 2/2015 | Rentas .................. G06F 19/366 705/3 |
| 2015/0088536 A1 | 3/2015 | Thelen et al. |
| 2015/0269344 A1 | 9/2015 | Repko |

(Continued)

*Primary Examiner* — Jason S Tiedeman
(74) *Attorney, Agent, or Firm* — CALFEE, HALTER & GRISWOLD LLP

(57) ABSTRACT

A server computing device has data stored thereon, where such data includes identities of multiple participants in a care plan of a patient, the care plan identifies multiple health attributes of the patient that are to be monitored by the multiple participants. The data also includes roles of the multiple participants in the care plan of the patient, the roles respectively identify which of the health attributes is to be monitored by which participant in the multiple participants. The server computing device is further programmed to, in response to receipt of a request from a client computing device operated by the patient, cause content to be presented in a graphical user interface on a display of the client computing device, the content comprises the identities of the multiple participants in the care plan of the patient and the roles of the multiple participants in the care plan of the patient.

20 Claims, 17 Drawing Sheets

(56) References Cited

U.S. PATENT DOCUMENTS

| | | | |
|---|---|---|---|
| 2015/0379204 A1* | 12/2015 | Douglass | G16H 10/60 705/3 |
| 2016/0085927 A1 | 3/2016 | Dettinger et al. | |
| 2016/0098536 A1 | 4/2016 | Dettinger et al. | |
| 2016/0098538 A1 | 4/2016 | Dettinger et al. | |
| 2016/0188821 A1 | 6/2016 | Ozeran | |

* cited by examiner

My Health Campaign

Signed in as Dr. Jerry Atchin's          Settings

302

Campaign Access Manager

[ Join ]    [ Invite ]

Updated: 3 days ago by Mary Smith

304

Mrs. Mary Smith
Female
13-MAR-1951 (58 years old)
Payers: BCBS

| Home Address: | Phone: 919-555-5555 | Race: White |
|---|---|---|
| 3554 North Shallowford Road | Email: MarySmith58@yahoo.com | Ethnicity: Jewish |
| Raleigh, NC 27612 | | 306 |

John Gilpin — Mary's Wellness Coach — Contributed: 1 day ago

Dr. Joy Jackson, MD — Mary's Family Doctor — Contributed: 2 weeks ago

Miranda Mitchell, RN — Mary's Diabetic Educator — Contributed: 2 weeks ago

Dr. Eli Thomas, Psy.D — Mary's Psychiatrist — Contributed: 1 month ago

Dr. Joy Jackson, MD — Mary's Nutritionist — Contributed: 3 months ago

Dr. Jerry Atchins, MD — Mary's Endocrinologist — Contributed: 3 months ago

308     My Health     310

Hi there. I am a 58 year old married grandmother with 2 children and 1 grandchild. I have had Type 1 diabetes since I was 11 years old. I have been using an Omnipod Insulin Pump for the last 10 years and generally take good care of myself. I recently developed Hypothyroidism and have started taking Synthroid to alleviate symptoms. I have had a lot of stress recently as my husband has developed Melanoma and grandchild has been diagnosed with Autism. As a result, I am actively being treated for Depression. I recently began taking Yoga and Tai-Chi classes through RDU Wellness Center, which, is helping me feel better and improving my blood sugars.

Revision History (4): View   Comments (6) View | Add — 318

312   314   316

[ Goals ] [ Problems & Conditions ] [ Measures and Observations ] [ Prescriptions ]

Manage: Subscriptions | Publications     [ ⊕ Add Health Item ]

FIG. 3

Revision History (4): View   Comments (6) View | Add

| Goals | Problems & Conditions | Measures and Observations | Prescriptions |

Manage: Subscriptions | Publications   _316_   ⊕ Add Health Item

Blood Sugar   ☑ Subscribe
Glucose Test Strips Rx

404

| Last Report | Next Report |
| 136 mg/dL | Every day, before and after meals and at bedtime |
| Today at 1:15 PM | *Monitored by* Dr. Joy Jackson, MD |
| *Reported by* Mrs. Mary Smith | ⊕ Add   —402 |

3,420 Reports

3 Month Blood Sugar Average   ☑ Subscribe
HbA1c (Overdue)

| Last Report | Next Report |
| 7.8 % | OVERDUE Due on 01-MAR-2015 |
| 01-DEC-2015 | |
| *Reported by* Dr. Jerry Atchins, MD | ⊕ Add |

38 Reports

Thyroid Producing Hormones   ☑ Subscribe
TSH  (Overdue)

| Last Report | Next Report |
| 12.6 mIU/L | OVERDUE Due on 01-MAR-2015 |
| 01-DEC-2015 | |
| *Reported by* Dr. Jerry Atchins, MD | ⊕ Add |

16 Reports

| Cholesterol Levels<br>Lipid Panel | | ☑ Subscribe |
|---|---|---|
| « <br>31 Reports | Last Report<br>HDL<br>12.6<br>16-FEB-2015<br>*Reported by*<br>Dr. Joy Jackson, MD | Next Report<br>Due on: 16-MAY-2015<br>*Managed by*<br>Dr. Joy Jackson, MD<br>⊕ Add |
| « <br>31 Reports | Last Report<br>LDL<br>12.6<br>16-FEB-2015<br>*Reported by*<br>Dr. Joy Jackson, MD | Next Report<br>Due on: 16-MAY-2015<br>*Managed by*<br>Dr. Joy Jackson, MD<br>⊕ Add |
| « <br>31 Reports | Last Report<br>Triglycerides<br>12.6<br>16-FEB-2015<br>*Reported by*<br>Dr. Joy Jackson, MD | Next Report<br>Due on: 16-MAY-2015<br>*Managed by*<br>Dr. Joy Jackson, MD<br>⊕ Add |

FIG. 4A

Contributors (6)

| John Gilpin | Dr. Joy Jackson, MD | Miranda Mitchell, RN |
|---|---|---|
| Mary's Wellness Coach | Mary's Family Doctor | Mary's Diabetic Educator |
| Contributed: 1 day ago | Contributed: 2 weeks ago | Contributed: 2 weeks ago |
| Dr. Eli Thomas, Psy. D | Dr. Joy Jackson, MD | Dr. Jerry Atchins, MD |
| Mary's Psychiatrist | Mary's Nutritionist | Mary's Endocrinologist |
| Contributed: 1 month ago | Contributed: 3 months ago | Contributed: 3 months ago |

◁ Contributor Details ▷     [Close]

I am currently providing care    [Edit]

500

Dr. Jerry Atchins, MD
Mary's Endocrinologist

| Seen for | Last saw | Pledged support | Next appointment |
|---|---|---|---|
| 6+ years | 3 months ago | 2 years ago | ? |
| First encounter May 2013 | Last encounter April 4, 2015 | Joined campaign May 2014 | Not scheduled |

Monitoring   [View] [Edit]
Diagnoses of Type 1 Diabetes
Diagnoses of Hypothyroidism

Reporting   [View] [Edit]
Results for HbA1c (3 month blood sugar)
Results for TSH (Thyroid Hormones)
Results for HDL LDL Triglycerides (Cholesterol)

Managing   [View] [Exit]
Prescription for Novolog Insulin
Prescription for Test Strips
Prescription for Omnipod Insulin Pump
Prescription for Synthroid

Subscriptions   [View] [Edit]
3 of 3 Problems
2 of 2 Goals
2 of 2 Measures
5 of 5 Prescriptions

Published   [View] [Add]
1 Problems
1 Goal
79 Measures
14 Prescriptions

Contact

Copper Woods Endocrine Associates
555 Healthy Way
Suite 5
Raleigh NC 5555

[Send Message] [Edit]
Phone: 919-999-5555
Fax: 919-999-5544
www.reraleigh.com

FIG. 5

Campaign Access Manager

○ Health Provider  ○ Family Member/Other

I want to invite a...

Find Health Provider

Health Provider's Name

First Name [ ]   Last Name [ Hancock ]

Health Provider's Location

[ United States ▼ ]

City [ ]   State [ North Carolina ▼ ]   Zip [ ]

[ Cancel ]   [ Clear Search ]

Results  _702_

| Name and Specialty | Address | Phone | _704_ |
|---|---|---|---|
| John Hancock<br>Allopathic & Osteopathic Physicians<br>NIP:1841268200 | 2709 Blue Ridge Road<br>Suite 320<br>Raleigh, NC | (919) 986-2457 | [ Select ] |

Campaign Access Manager

Campaign Invitation

Send to ← 802

| Name and Specialty | Address | Phone |
|---|---|---|
| John Hancock<br>Allopathic and OsteopathicPhysicians<br>NIP:1841268200 | 2709 Blue Ridge Road<br>Suite 320<br>Raleigh, NC | (919) 986-2457 |

How do you know John Hancock?

804 — ⦿ I am a patient    Date of last visit? <u>Add date</u>    How long have you been seeing?

806 — ○ I am a colleague

808 — ○ Other Comments: [            ]

810 — ○ Allow John Hancock to view and subscribe to this campaign.

812 — ⦿ Allow John Hancock to view, subscribe, and contribute information to this campaign.

Include personalized message (optional)

[                                            <u>814</u>  ]

By sending this invitation, you agree that you have read and authorized the <u>Release of Information</u>:

[ Cancel ]    [ Agree and Send Invitation ]
  816              818

FIG. 8

Your Contributions

→ 1100

View settings

Health Goals

| Patient Problems/Conditions | Team participation | Your participation | Your posting options | Subscribe |
|---|---|---|---|---|
| Maintain Weight <br> View details | 1 author <br> 4 monitoring | Select ▼ | Select ▼ | ☐ |
| Decrease frequency of abnormal blood sugar levels <br> View details | 1 author <br> 4 monitoring | Select ▼ | Select ▼ | ☐ |
| ⊕ Add | | | | |

Problems and Conditions

| Patient Problems/Conditions | Team participation | Your participation | Your posting options | Subscribe |
|---|---|---|---|---|
| Type 1 Diabetes | 5 monitoring | Select ▼ | Select ▼ | ☐ |
| Hypothyroidism | 3 monitoring | Select ▼ | Select ▼ | ☐ |
| Depression | 4 monitoring | Select ▼ | Select ▼ | ☐ |
| ⊕ Add | | | | |

Measures and Observations

| Measures/Observations | Team participation | Your participation | Your posting options | Subscribe |
|---|---|---|---|---|
| HbA1C | ✶ 2 reporting | Select ▼ | Select ▼ | ☐ |
| TSH | 1 reporting | Select ▼ | Select ▼ | ☐ |
| HDL | ✶ 2 reporting | Select ▼ | Select ▼ | ☐ |
| HDL | ✶ 2 reporting | Select ▼ | Select ▼ | ☐ |
| HDL | ✶ 2 reporting | Select ▼ | Select ▼ | ☐ |
| ⊕ Add | | | ✶ Indicates possible duplication of services | |

Prescriptions

Fig. 11

| Medications | Team participation | Your participation | Your posting options | Subscribe |
|---|---|---|---|---|
| Novolog<br>Insulin, Aspart, Human 100 UNT/ML Injectable Solution<br>View details | 1 managing | Select ▽ | Select ▽ | ☐ |
| Synthroid<br>Levothyroxine Sodium 0.15MG Oral Tablet<br>View details | ✱ 2 managing | Select ▽ | Select ▽ | ☐ |
| Zoloft<br>Sertraline 100 MG Oral Tablet<br>View details | 1 managing | Select ▽ | Select ▽ | ☐ |
| Other | Team participation | Your participation | Your posting options | Subscribe |
| Glucose Test Strips<br>Abbot Freestyle Lite, 50/bx, 4 boxes<br>View details | 1 managing | Select ▽ | Select ▽ | ☐ |
| Insulin Pump Supplies: Infusion Set<br>Omnipod System 10/bx, 4 boxes<br>View details | 1 managing | Select ▽ | Select ▽ | ☐ |

⊕ Add     ✱ Indicates possible duplication of services

Your Relationship

1. How long have you been seeing Mary Smith?

From  Add date of first encounter     To  Add date of last encounter

2. How do you want your elationship displayed?

I am Mary's OBGYN     Edit

Done

FIG. 11A

COMPUTING SYSTEM CONFIGURED FOR AGGREGATING AND DISPLAYING DATA

BACKGROUND

A care plan for a patient provides direction on a type of care the patient may need over time, where the care plan is typically defined by a care provider. For instance, a care plan can be as simple as the care provider (e.g., a general practitioner) keeping track of when the patient is next due for an immunization. In another example, a care plan can be relatively complex, such as a detailed plan for an oncology patient that covers diet, chemotherapy, radiation, lab work, and counseling, where the care plan includes detailed timing relationships, preconditions, and goals. Thus, scope of care plans may vary widely—exemplary care plans include 1) multidisciplinary, cross-organizational care plans (e.g., an oncology plan including an oncologist, home nursing staff, pharmacy, and others); 2) care plans to manage a specific disease/condition (e.g. a nutritional plan for a patient post bowel resection, a neurological plan post head injury, a prenatal plan, a postpartum plan, a grief management plan, etc.); 3) decision-support generated plans that follow specific practice guidelines (e.g., a stroke care plan, a diabetes plan, a falls prevention plan, etc.); 4) a care plan that includes a care team, including roles associated with a particular condition or set of conditions; 5) a self-maintained patient plan that identifies goals of the patient and an integrated understanding of actions to be taken to meet the goals; or some suitable combination of the exemplary plans set forth above.

Conventionally, a care plan is generated at the point of care by a care provider (e.g. a clinician). Typically, the care plan is generated in association with a care event, which can be defined as can interaction with a care provider at a location and in an environment with respect to at least one health attribute of the patient. Care events are typically associated with care episodes, where a care episode spans some defined length of time and includes multiple documented care events (which may be associated with different care providers). The care plan may also include a high-level problem context assigned to the patient, wherein such context can be assigned to a care episode or to care events individually.

Various problems currently exist with respect to computing technologies employed to administer a care plan for a patient. To illustrate at least some of the problems, an example is set forth that demonstrates a prototypical health experience of a patient with a complex chronic health profile. Specifically, a patient with Type I diabetes and hypothyroidism may receive care from both a primary care physician (PCP) as well as an endocrinologist. Oftentimes, both of these clinicians may attempt to monitor and manage the same health attributes, providing an unnecessary duplication of services (e.g., both clinicians may order an A1C test). Computing systems used in the healthcare environment are incapable of allowing providers to readily ascertain what has been done by other providers participating in the care plan. When computing systems in healthcare environments communicate with each other electronically, such communication is undertaken through structured data, wherein the structured data corresponds to encounter event documents. Typically, this structured data is difficult to interpret by patients (and clinicians). Further, direct communications between care providers in different (or even the same) organizations are rare, as such direct communications entail a relatively large cost in coordinating this information verbally between two separate offices.

From the patient perspective, the patient becomes ultimately responsible for ensuring adherence to the care plan, and thus must communicate clinical knowledge about medication periodicity, test results, blood measures, etc. between clinicians. As the patient must communicate this information to clinicians at the point of care, time is lost, as the clinician must adjust downstream evaluation procedures on the spot, rather than ahead of time. Conventional computing systems accessible to a patient are also ill-equipped to facilitate exchange of information between participants in the care plan. An exemplary application that is accessible to a patient is referred to as a patient portal. The patient portal is configured to collect health information about a particular user. This information, however, tends to be set forth in silos, in that the information is not readily accessible to different care providers.

Therefore, using conventional computing systems, when visiting a care provider in the care plan for a care event, the patient must take her computer, access a network of the care provider, and describe to the care provider what the patient has entered or retrieved by way of the patient portal. Alternatively, the patient may take a journal that includes handwritten information, a flash drive that includes a file about the care plan of the patient, etc. The provider then reviews the information set forth by the patient (which may or may not be trusted by the provider), and then provides care based upon such information.

SUMMARY

The following is a brief summary of subject matter that is described in greater detail herein. This summary is not intended to be limiting as to the scope of the claims.

Described herein are various technologies pertaining to a computing system that is configured to readily allow information to be transmitted between computing devices operated by participants in a care plan for a patient, where the participants include the patient, care providers, a legal representative of the patient, family and friends of the patient, etc. In an exemplary embodiment, a server computing device may execute a care plan application. Generally, the server computing device, when executing the care plan application, can be configured to: 1) define parameters of a care plan for a patient (based upon data received from one or more of the participants in the care plan); 2) update information in the care plan based upon data received from computing devices of participants in the care plan; 3) assign and enforce roles for participants in the care plan (e.g. define who is allowed to update which type of data in the care plan, define who is allowed to review certain information in the care plan, etc.), and so forth. The care plan application can also be configured to retrieve data pertaining to the care plan of the patient. In a non-limiting example, an electronic health record application (EHR) may execute in a computing environment utilized by a care provider in the care plan, and the care provider may update information about the care plan by way of the EHR. The EHR may expose data to a health information exchange (HIE), which can format the data and store the data in computer-readable storage. The care plan application can be configured to retrieve information from this computer-readable storage and update the care plan to include the data. Further, a computing device operated by another care provider in the care plan may not have an EHR executing thereon. Instead, the care provider may generate an e-mail directed to an email address corresponding to the care plan application. The care plan application can update information in the care plan of the patient based upon such e-mail. For instance, the care plan application may be configured to receive content of the e-mail, extract relevant information therefrom (e.g. through natural language processing techniques or based upon a predefined schema, etc.), and the care plan application may update the care plan with the extracted information.

The care plan application may receive updated information about the care plan from any suitable source. In other words, the care plan application allows for information about the care plan to be provided in a crowd-sourced manner from any computing device operated by any participant in the care plan.

The care plan application executing on the server computing device is also configured to provide appropriate information to a computing device operated by a participant in the care plan upon receipt of a request from such computing device. For instance, a mobile telephone may be operated by the patient in the care plan, and the mobile telephone may be instructed to communicate with the server computing device that executes the care plan application (e.g., by way of a browser, by way of a dedicated client application executing on the mobile telephone, etc.). The request from the mobile telephone may include information that is indicative of the identity of the patient (such as a username and password). The care plan application receives this information and retrieves information about the care plan that is to be provided to the patient. This information is then transmitted from the server device to the mobile telephone where it can be consumed by the patient.

Further, it is to be understood that the information provided to the patient is customized for the patient (e.g., the information provided to the patient is not the same as the information that would be provided to another participant in the care plan). The information provided to the patient may identify goals of the patient with respect to at least one health attribute, conditions diagnosed for the patient, upcoming appointments of the patient pertaining to the care plan, medications prescribed to the patient, and so forth. Further, the information provided to the patient can include identities of other participants in the care plan, including care providers and their roles in the care plan.

Contrarily, a computing device operated by a care provider in the care plan may be directed to the server that executes the care plan application, wherein the computing device transmits a request for care plan information to the care plan application executing on the server device. This request may include an identity of the care provider, as well as an identity of the patient. In response to receiving the request, the care plan application can cause care plan information customized for the care provider to be transmitted to the computing device operated by the care provider. This information can include, for instance, tasks to be performed by the provider with respect to the care plan of the patient (such as tests to be performed, tests previously performed, and so forth), identities of other participants in the care plan and their corresponding roles, identities of other tasks that are to be performed by other care providers in the care plan (so that duplication of services is avoided), a role of the provider in the care plan, and so forth.

Various graphical user interface features are also presented herein that facilitate this exchange of information between computing systems, as well as the formatting of information for consumption by participants in the care plan. These graphical user interfaces can include graphical user interfaces configured for presentment on larger screens (e.g., 12 inches and larger), graphical user interfaces for presentment on medium-sized screens (e.g. between 8 inches and 12 inches), as well as graphical user interfaces configured for presentment on smaller screens (between 4 inches and 8 inches). Further, one or more features depicted in the graphical user interfaces disclosed herein may be presented on screens on wearable devices such as portable watches, head mounted displays, and so forth.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 3 illustrates an exemplary graphical user interface that is well-suited for presentment to a care provider identified in a care plan of a patient.

FIG. 4 illustrates another exemplary graphical user interface that is well-suited for presentment to a care provider identified in a care plan of a patient.

FIG. 5 illustrates an exemplary graphical user interface that depicts information about a care provider in a care plan of a patient.

FIG. 7 is a graphical user interface that illustrates addition of a clinician as a care provider to a care plan of a patient.

FIG. 8 is a graphical user interface that depicts an invitation provided to an individual, wherein the invitation is configured to invite the individual to be added as a participant in a care plan of a patient.

FIG. 11 is a graphical user interface that is well-suited for presentment to a care provider in a care plan.

DETAILED DESCRIPTION

Figure 1:
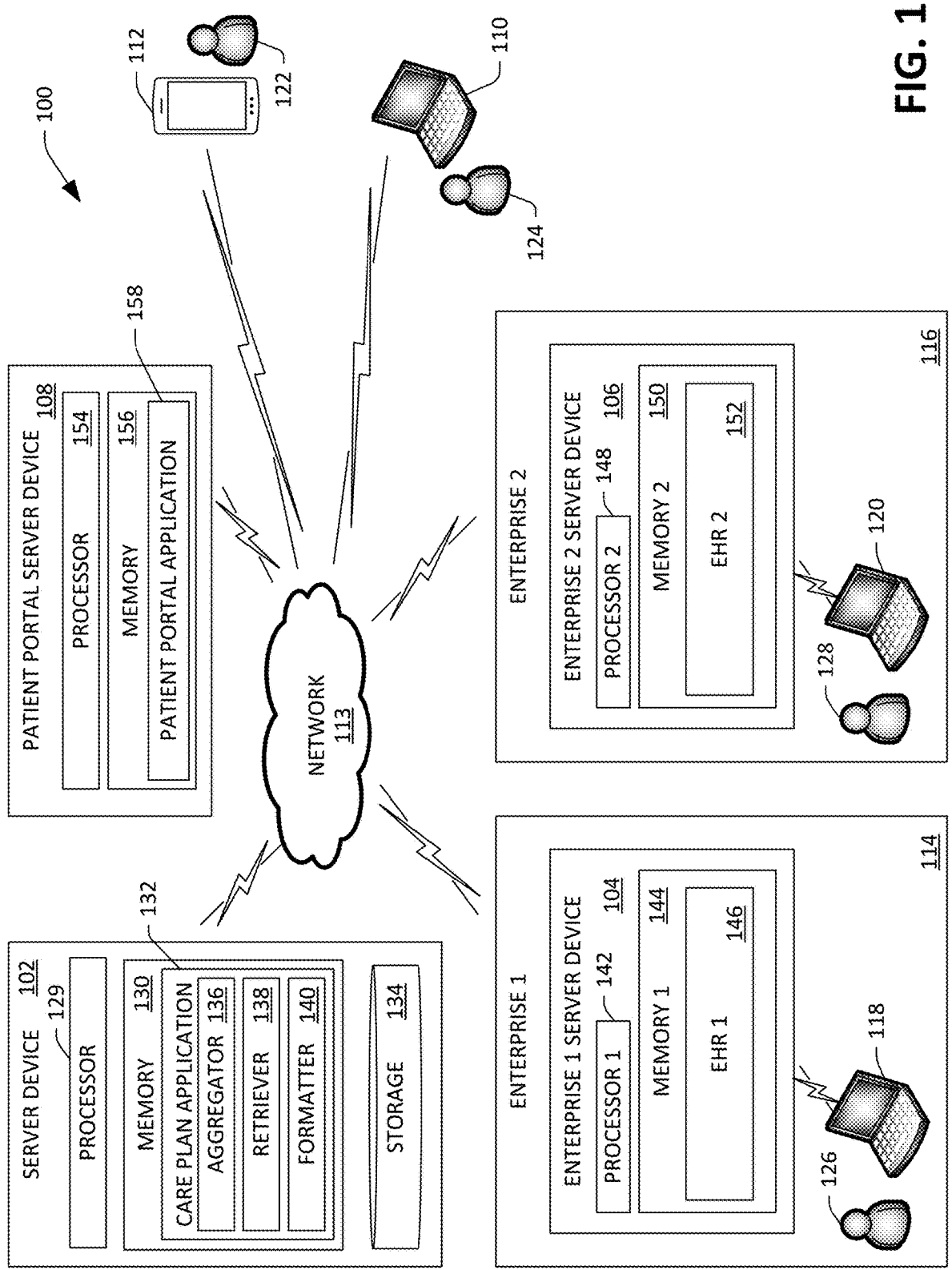
FIG. 1 is a functional block diagram of an exemplary system that facilitates exchanging information between computing devices operated by participants in a care plan of a patient.

Various technologies pertaining to generating an electronic care plan for a patient and updating the care plan for the patient based upon received from computing devices operated by multiple participants in the care plan are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference now to FIG. 1, an exemplary system 100 that facilitates exchanging information between computing devices operated by participants in a care plan of a patient is illustrated. A care plan provides direction on the type of care a patient may need. A care plan will typically include a goal or set of goals about a health attribute of a patient, where the goals or set of goals are often set forth by a care provider at the point of care. The care plan may also include other information about at least one health attribute of the patient, such as a diagnosis, an identity of the health attribute that is to be monitored, and so forth. The care plan assists care plan participants (including the patient) in causing the patient (and possibly other participants) to adhere to the care plan, such that the patient can reach the goals specified in the care plan. A participant in the care plan can be any person or legal entity that participates in the care plan of the patient. Therefore, for example, a participant in the care plan may be a care provider, the patient, a friend or family member of the patient, a legal representative of the patient, etc. A care plan provider is a provider of care for the patient with respect to at least one health attribute identified in the care plan. For instance, a care plan provider may be a clinician (a doctor, psychiatrist, nurse, etc.), a wellness coach, an educator, or the like.

As noted previously, participants in a care plan may be spread over several different organizations, where the organizations utilize different computing systems when providing care to the patient. For instance, a care plan for a patient may be a multidisciplinary, cross-organizational care plan, wherein participants in the care plan include an oncologist, a home nurse, and a pharmacy. As noted above, conventional computing systems are incapable of exchanging care plan information between computing devices operated by the patient of the care plan and care plan participants.

The system 100 described herein cures these deficiencies. The system 100 includes a server computing device 102, a server computing device 104 in a first enterprise 104 (referred to hereafter as the first server computing device 104), a server computing device 106 in a second enterprise 106 (referred to hereafter as the second server computing device 106), a patient portal server device 108, a client computing device 110, and a client computing device 112. The computing devices 102-112 are in communication with one another by way of a network 113. The first server computing device 104 is shown in FIG. 1 as belonging to or being controlled by a first enterprise 114 (e.g., a first healthcare organization, a first doctor's office, etc.), while the second server computing device 106 is shown as being owned or controlled by a second enterprise 116 (a second healthcare organization, a second doctor's office, etc.). The first enterprise 114 further includes a client computing device 118 that is in communication with the first server computing device 104, and the second enterprise 116 further includes a client computing device 120 that is in communication with the second server computing device 106.

In the exemplary system 100 shown in FIG. 1, the client computing device 112 is operated by a patient 122 who is the subject of a care plan, the client computing device 110 is operated by first participant 124 in the care plan, the client computing device 118 is operated by a second participant 126 in the care plan, and the client computing device 120 is operated by a third participant 128 in the care plan.

The server computing device 102 includes a processor 129 and memory 130, wherein the memory 130 has a care plan application 132 loaded therein that is executed by the processor 129. The server computing device 102 also includes a data storage device 134 which can persistently retain data about care plans for patients. Generally, the care plan application 132, when executed by the processor 129, is configured to perform at least the following functions: 1) define initial parameters of a care plan for the patient 122 in response to receipt of instructions from a computing device operated by one of the participants 122-128 in the care plan of the patient 122 (where the patient 122 is also a participant); 2) generate and transmit electronic invitations to computing devices operated by individuals who are to be added as participants to the care plan; 3) define roles for participants in the care plan, wherein a role of a participant can define information that is to be accessible for review by the participant, information that can be added to the care plan by the participant, information in the care plan that can be edited by the participant, etc.; and 4) transmit appropriate information about the care plan to a participant as a function of the identity of the participant and the participant's role in the care plan.

To perform at least these functions referenced above, the care plan application 132 can include: an aggregator component 136 that is configured to aggregate information pertaining to the care plan that has been generated at computing devices operated by participants in the care plan; a retriever component 138 that is configured to retrieve information about the care plan in response to receipt of a request for such information from a client computing device operated by a participant in the care plan; and 3) a formatter component 140 that is configured to receive information generated at a computing device operated by a participant in the care plan and format the data appropriately for storage in the storage device 134. Operation of the care plan application 132 and its components 136-140 will be described in greater detail below. Generally, however, it is to be understood that the care plan application 132 can be perceived as leveraging the paradigm of crowd-sourcing to acquire data, thereby allowing all participants in the care plan (including the patient) to review and contribute to the care plan of the patient in a uniform manner.

To describe functionality of the care plan application 132, the exemplary architecture depicted in FIG. 1 is employed to set forth various examples. It is to be understood, however, that this architecture is not intended to limit the scope of the features described herein. In the exemplary architecture shown, the first server computing device 104 includes a processor 142 and memory 144, wherein a first electronic health record application (EHR) is stored in the memory 144 and is executed by the processor 142. The second server computing device 106 includes a processor 148 and memory 150, wherein the memory 150 has stored therein a second EHR 152 that is executed by the processor 148. It is to be understood that the first EHR 146 and the second EHR 152 can be entirely different applications that are not configured to electronically communicate with one another. Each of the EHRs 146 and 152 can be configured to perform various health-related tasks including task related to patient intake, invoicing, diagnosis, prescriptions, etc.

The patient portal server device 108 includes a processor 154 and memory 156, wherein a patient portal application 158 is stored in the memory 156 and executed by the processor 154. The patient portal application 158 is a patient facing application that may provide the patient 122, by way of the client computing device 112, access to health information about the patient 122. Such information can include information about invoices due to an organization, tests performed on the patient 122 over some period of time, medications prescribed to the patient 122, and other health information about the patient 122. The patient portal application 158 may interface with the first EHR 146, the second EHR 152, both of the EHRs 146 and 152, or neither of the EHRs 146 and 152. The computing device 110 may fail to have installed thereon or interface with either an EHR or the patient portal application 158. For instance, the computing device 110 may be operated by a wellness coach that does not use an EHR when providing care to clients. Further, the computing device 110 may be prevented from interfacing with either of the EHRs 146 or 152, and may be prevented from accessing information about the patient 122, generated and maintained by way of the patient portal application 158. From the foregoing, it can be ascertained that the computing system 100 is a complex system, where different applications installed computing devices may not be configured to electronically communicate with one another.

Defining Initial Parameters of a Care Plan

Operation of a subset of the computing devices shown in FIG. 1 when initial parameters of a care plan of the patient 122 are defined is now described. In an example, the patient 122 may visit the first enterprise 114, and may see a clinician (who will become the participant 126 in the care plan of the patient 122). At the point of care, the clinician 126 may choose to generate a care plan for the patient 122. To do so, the participant 126 operates the computing device 118 to transmit data to the first server computing device 102, which in turn causes data to be transmitted to the server computing device 102 that executes the care plan application.

In non-limiting examples, the clinician may cause a web browser to be executed on the client computing device 118, and may direct the web browser to a uniform resource locator (URL) corresponding to the care plan application 132. The care plan application 132, when executing on the server device 102, may then cause the server device 102 to transmit data to the computing device 118 that is configured to facilitate generation of a care plan for a patient (e.g., the patient 122). In another example, the computing device 118 may have a client-side application installed thereon that is specific to the care plan application 132, and is configured to interface with the care plan application 132. This client-side application can be executed at the client computing device 118, where it can communicate with the care plan application 132 to facilitate creation of a care plan for the patient 122.

Further, this client-side application, in an example, may be a plug-in to a client-side application that is executable at the client computing device 138, wherein the client-side application is configured to communicate with the first EHR 146 (e.g., the client-side application is specific to the EHR). For example, this client-side application may be executing on the client computing device 118, and may have a graphical user interface that comprises a button, that, when selected, initiates the plug-in (in the context of the client-side application that is specific to the EHR). An advantage to this approach is that the clinician does not have to learn an entirely new GUI—any UI features corresponding to the care plan application 132 can be presented in the context of the first EHR 146. Further, the clinician need no exit or minimize the client-side EHR application with which the clinician interacts when providing care to patients.

In any of these embodiments, the clinician, in communication with the patient 122, can operate the client computing device 118 to define parameters for a care plan for the patient 122. These parameters can include goals for the patient, health attributes of the patient 122 to monitor (which may include measurable attributes (such as blood sugar levels), conditions (such as a state of depression), diagnoses, etc.), identities of other individuals who are to participate in the care plan, etc. In a detailed example, at the point of care, the patient 122 may indicate to the clinician that she has had Type I Diabetes since she was eleven years old, and has been using a certain type of insulin pump for the last ten years. The patient 122 may also have recently developed Hypothyroidism and started taking a particular medication to alleviate symptoms. The patient 122 may further indicate that she is being treated for depression and has started taking certain exercise classes to improve the condition and improve blood sugar levels. Based upon this information, the clinician may operate the client computing device 118 to set forth parameters of the care plan, which may include goals for the patient 122, identities of problems and conditions for the patient 122, any observations about the patient 122 made by the clinician, and any prescriptions for the patient 122 known by the clinician or prescribed by the clinician. The client computing device 118 can be caused to transmit such information to the server computing device 102 by way the network 113 (potentially by way of the first server computing device 104), and the care plan application 132 can construct a care plan with the defined parameters and cause such care plan to be retained in the memory 130 and/or the storage device 134. Since the clinician created the care plan, the clinician can be identified in the care plan as being the manager of the care plan.

Inviting Individuals to Become Participants in the Care Plan

Once the care plan application constructs the care plan 132 (with the parameters defined by the clinician and/or the patient 122), the clinician becomes the participant 126 in the care plan. When the initial parameters for the care plan are defined or time later, the participant 126 and/or the patient 122 may wish to invite other individuals to become participants in the care plan for the patient 122. For instance, the participant 126 may be the family doctor for the patient 122. As indicated previously, the patient 122 may have developed hypothyroidism. Thus, it may be desirable to invite an endocrinologist to become a participant in the care plan of the patient 122. As noted previously, either the patient 122 or the participant 126 (since the participant 126 is the manager of the care plan) may operate a computing device to construct an invitation that is to be sent to a computing device operated by an endocrinologist.

In an example, the participant 126 can operate the computing device 118 such that the computing device 118 is placed in communication with the server computing device 102 that executes the care plan application 132 executing on the server device 102. The participant further operates the client computing device 118 to identify an endocrinologist, and indicate to the care plan application 132 the identity of the endocrinologist. For instance, the participant 128 may be an endocrinologist that practices at the second enterprise 116. The care plan application 132 receives the identity of the endocrinologist (e.g., an e-mail address of the endocrinologist) as well as an identity of the patient 122. The care plan application 132 may then cause the server computing device 102 to direct an invitation to the e-mail address (or other electronic alias) of the endocrinologist, where the invitation invites the endocrinologist to become a participant in the care plan for the patient 122. The endocrinologist, when operating the client computing device 120, can be provided with the invitation, wherein the invitation can identify: 1) the prospective role of the endocrinologist in the care plan; 2) the patient 122; 3) other participants in the care plan; and 4) permissions the endocrinologist will have in the care plan.

The invitation can include selectable options to accept or decline the invitation. When the endocrinologist selects the button to accept the invitation, then data is transmitted from the client computing device 120 to the server computing device 102 indicating that the endocrinologist has accepted the invitation and is now a participant (the participant 128) in the care plan application (with the role and permissions identified in the invitation).

In an exemplary embodiment, when the computing device 120 operated by the participant 128 fails to have a client-side application installed thereon that is dedicated to the care plan application 132 (e.g., similar to the plug-in described above), the participant 128 can be provided with an option (e.g., in the invitation) to install such a client-side application on the client computing device 120. Again, in an example, this client-side application may be installed as a plug-in to a client-side application installed on the client computing device 120 that interfaces with the second EHR 152 executing on the second server computing device 106. When the computing device 120 already has a client-side application installed thereon that is dedicated to the care plan application 132, rather than receiving an e-mail message that includes an invitation, the computing device 120 can receive a push notification that may be presented in the context of the client application that interfaces with the second EHR 152. The role assigned to the endocrinologist in the invitation can also indicate whether or not the endocrinologist is able to invite others to the care plan for the patient 122.

Further, as indicated previously, the patient 122 may be taking exercise classes, and therefore the patient 122 and/or the participant 126 may wish to invite a wellness coach to become a participant in the care plan. In an example, the patient 122 can operate the computing device 112 to cause an invitation to be directed to an email address (or other electronic alias) of the wellness coach. The wellness coach can receive the invitation when operating the client computing device 110.

For instance, the client computing device 112 operated by the patient 122 may have a mobile application executing thereon that is specific to the care plan application 132. By way of this mobile application, the patient 122 can set forth data that identifies the wellness coach (an electronic alias for the wellness coach), and can define a role of the wellness coach in the care plan. The care plan application 132 receives this data, and then directs an invitation (with the defined role) to the electronic alias of the wellness coach. This invitation is eventually received at the computing device 110 when operated by the wellness coach, where the wellness coach can accept the invitation and be added as a participant to the care plan of the patient 122 (with the role set forth in the invitation). As described above, the invitation may include a link that, when selected, causes a client-side application to be installed on the client computing device 110, wherein such application is configured to interface with the care plan application 132 executing on the server computing device 102. Alternatively, a browser executing on the client computing device 110 can interface with the care plan application 132. From the foregoing, it can be ascertained that invitations can be provided to various care plan participants who operate computing devices that are not configured to communicate directly with one another.

Updating the Care Plan

Participants in the care plan, depending upon permissions assigned thereto, can utilize their respective computing devices to update the care plan of the patient 122. For example, the patient 122 may visit the second enterprise 116 for an appointment with the endocrinologist, who is the participant 128 in the care plan of the patient 122. The endocrinologist may perform a test on the patient 122 and may wish to update the care plan of the patient based upon results of such test (to indicate in the care plan that the test has been performed and to further indicate measurements obtained from the test).

Several mechanisms for updating the care plan of the patient 122 are contemplated in this scenario. In a first example, an application may be installed on the client computing device 120, which may be a plug-in to a client side application that is specific to the second EHR (e.g., which interfaces with the second EHR 152 executing on the server device 106). The participant 128 may select a button in the graphical user interface of the HER, which can cause a graphical user interface for the plug-in to be presented. Data fields set forth in the graphical user interface of the plug-in can be populated with the test results and/or observations of the participant 128, and can be transmitted to the care plan application 132 from the client computing device 120.

In another example, the computing device 120 may have a client-side application installed thereon that is configured to communicate with the second EHR, but may not have an application installed thereon that is specific to the care plan application 132. In this example, the participant 128 may set forth data into the second EHR 152 by way of conventional means. The second server computing device 106 may also include a health information exchange (HIE) (not shown)

executing thereon, which can receive information exposed by the EHR 152 and format the information such that it can be interpreted by other applications. For example, the HIE may format data exposed by the EHR 152 in a standardized data format (to create formatted data), wherein such formatted data may be interpretable by the care plan application 132 (and used to update the care plan of the patient 122).

The aggregator component 136 can aggregate data exposed by the HIE (and other HIEs), and the retriever component 138 and can search this data for information pertaining to the patient 122. Upon locating data pertaining to the patient 122, the retriever component 138 can cause this data to be stored in the storage device 134 in association with the care plan of the patient. The care plan application 132 can therefore update the care plan based upon information that has been exposed by the HIE. In a third example, the client computing device 120 can execute a web browser, and the participant 128 may direct the web browser to a URL of the care plan application 132 executing on the server computing device 102. This can cause the browser to load a web page that interfaces with the care plan application 132, wherein the participant 128 can set forth user credentials (and optionally the identity of the patient 122). Subsequently, the participant 128 can set forth updates to the care plan of the patient 122 to the care plan application 132 by way of the web browser.

In yet another example, the second server computing device 106 can have another application executing thereon that monitors electronic communications generated by way of the second EHR 156. For instance, these communications can be formatted in accordance with a suitable standard, such as HL7. The another application can detect such communications (which may include information about the patient 122), and can provide information in these communications to the care plan application 132, whereupon the care plan application 132 updates the care plan of the patient 122. For example, the second EHR application 156 can be operated by the participant to cause an electronic communication (e.g., a facsimile) to be transmitted to a pharmacy, where the communication includes prescription information, and further where the communication has a standard format (e.g., HL7). The another application can detect such transmission, and can cause data in the transmission to be directed to the care plan application 132 executing on the server computing device 102. Alternatively, the second EHR 156 can be configured to relay data from the transmission to the care plan application 132 itself.

After the visit with the participant 126, the patient 122 may visit the wellness coach (the participant 124). The participant 124 may wish to update the care plan of the patient 122 with information pertaining to the exercises performed by the patient 122. In an example, the participant 124 may generate an e-mail that includes observations about the exercise routine of the patient 122 and can transmit the e-mail to an e-mail address corresponding to the care plan application 132. The formatter component 140 can analyze content of the e-mail and format such content so that the care plan of the patient 122 can be updated to reflect the content. For example, the formatter component 140 may use natural language processing techniques to extract information from the e-mail and cause such information to be stored in the storage device 134.

Subsequently, the patient 122 may wish to update her care plan with observations about a health attribute. In an example, the computing device 112 can be operated by the patient 122 to communicate with the patient portal application 158 executing on the patient portal server device 108. For instance, a browser on the computing device 112 may be directed to a URL that corresponds to the patient portal application 158. The patient portal application 158 may interface with the care plan application 132. Thus, information set forth into the patient portal application 158 by the patient 122 may be transmitted from the patient portal application 158 to the care plan application 132. These examples have been set forth to illustrate that the care plan of the patient 122 can be updated by many different participants in the care plan operating different computing devices in different computing contexts without requiring direct communication between computing devices operated by the participants in the care plan, which has heretofore not been possible.

Presenting Care Plan Information

The care plan application 132 is configured to present appropriate (potentially customized) care plan information to each care plan participant based upon the identity of the care plan participant and the role of the care plan participant in the care plan. For example, the patient 122 may return to the family doctor (the participant 126) at the first enterprise 114. At the point of care, the participant 126 may utilize the computing device 118 to retrieve information about the care plan of the patient 122 from the care plan application 132 executing at the server computing device 102. To do so, the participant 126 causes the computing device 118 to be in communication with the server computing device 102, such that data that identifies the participant 126 (and optionally data that identifies the patient 122) is transmitted to the server computing device 102 for receipt by the care plan application 132.

The care plan application 132, based upon this information, executes a query over content of the storage device 134 and retrieves appropriate care plan information that is to be presented to the participant 126. The care plan application 132 then causes the server computing device 102 to transmit the care plan information to the client computing device 118 for presentment on a display thereof. The care plan information presented on the display of the client computing device 118 can include information that is relevant to the participant 126 with respect to the care plan of the patient 122. This information may include, for example, data that indicates how long the participant 126 has been providing care for the patient 122, how long the participant 126 has been participating in the care plan of the patient 122, an indication of when the last time the participant 126 met with the patient 122, an indication of when the patient 122 is next scheduled to visit with the participant 126, identities of health attributes being monitored by the participant 126 in the care plan, identities of health attributes being reported on by the participant 126, identities of prescriptions being managed by participant 126, identities of types of information that is provided to the participant 126 in the care plan, identities of other participants in the care plan, and so forth. Again, this information is customized for each participant in the care plan when the participant accesses the care plan of the patient 122.

Further, as referenced above, this care plan information can be presented in the context of an EHR with which the participant 126 is already familiar. For example, by selecting a button in a graphical user interface that corresponds to the first EHR 146, when the participant 126 is providing care to the patient 122, information pertaining to the care plan of the patient can be presented in such graphical user interface.

Thereafter, the patient 122 may wish to view her progress in the care plan or set forth an update to information in the care plan. To do so, the patient 122 operates the client computing device 112 to place the client computing device 112 in communication with the server computing device 102, and causes the client computing device 112 to transmit authentication data for review by the care plan application 132 (e.g., username, password etc.). After determining that the patient 122 is authenticated to access data in the care plan of the patient 122, the care plan application 132 executes a query over data in the storage device 134 and returns the appropriate data in the care plan for the patient 122. This information may include, for instance, identities of participants in the care plan, identities of health attributes of the patient 122 being monitored by the participants in the care plan, roles of each participant in the care plan, wherein the roles identify which of the health attributes is to be monitored by which participant in the participants, tests conducted on the patient 122, results of such tests, steps taken to reach goals, medicines prescribed to the patient, and so forth. The care plan application 132 thereafter causes the server computing device 102 to transmit such information to the client computing device 112, and the client computing device 112 displays at least some of this information on a display thereof.

In summary, then, the care plan application 132 is configured to define parameters of a care plan for a patient and create an electronic care plan for the patent based upon such parameters. The care plan application 132 can allow multiple participants, who operate computing devices in different computing environments, to review and update the care plan, where each participant is provided with care plan information that is customized for that participant with respect to the patient 122.

Figure 2:
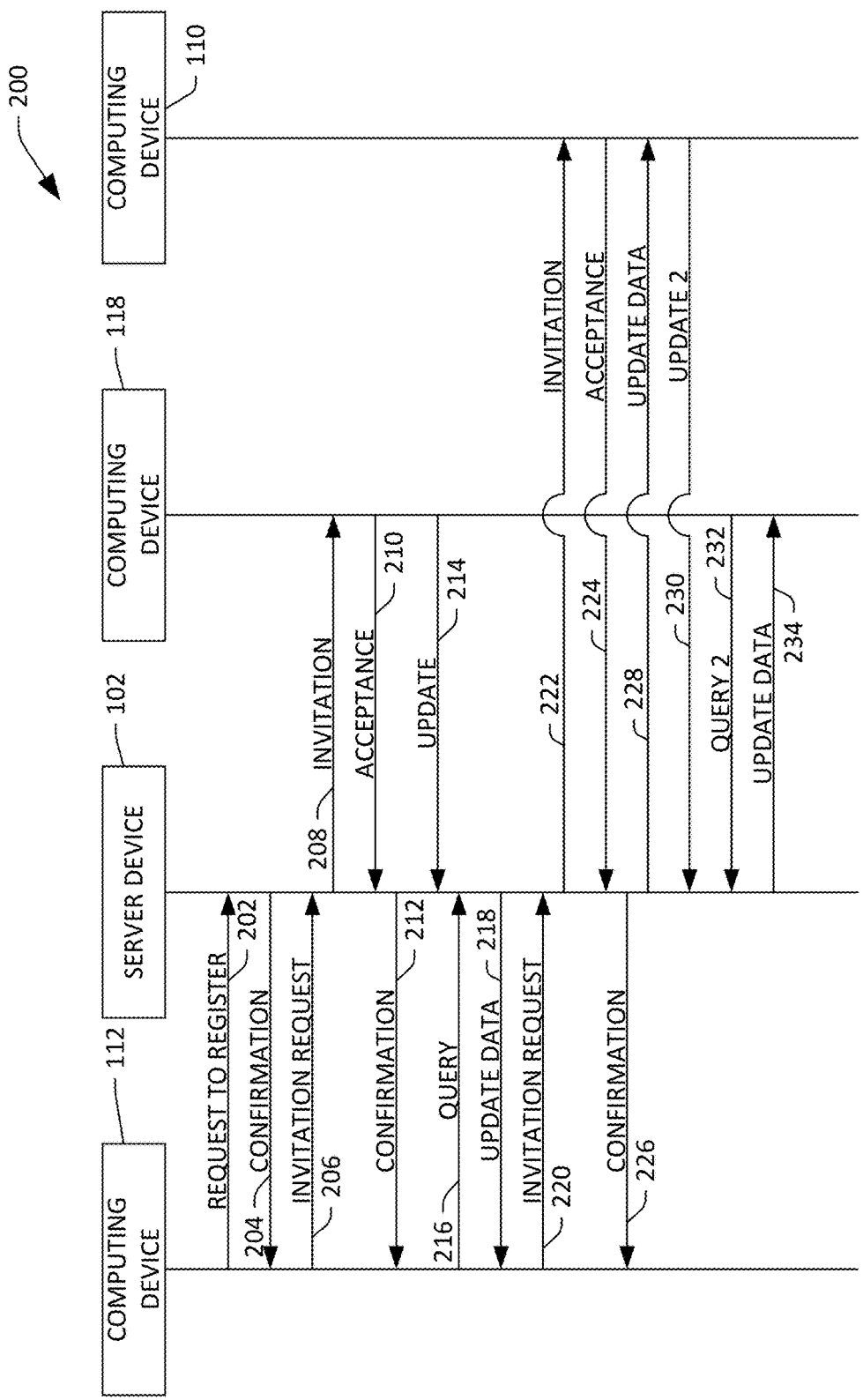
FIG. 2 is a control flow diagram that illustrates communications between computing devices operated by participants in a care plan of a patient.

Now referring to FIG. 2, an exemplary control flow diagram 200 is illustrated that depicts communications undertaken between the client computing device 112, the server computing device 102, the client computing device 118, and the client computing device 110 in connection with constructing and updating a care plan for the patient 122. At 202, the patient 122 operates the client computing device 112 to transmit a request to register with the care plan application 132 to the server computing device 102. This request, for instance, may include data that identifies the patient 122, health goals of the patient 122, medical issues of the patient 122, and so forth. The care plan application 132, executing at the server device 102, receives this request and constructs an electronic care plan for the patient 122. The server computing device 102, at 204, transmits a confirmation to the client computing device 112 that the patient 122 has registered with the care plan application 132.

At 206, the patient 122 operates the client computing device 112 to indicate that an invitation is to be transmitted to the family doctor (the participant 126). For instance, this indication can include an electronic identifier of the family doctor, such as an e-mail address of the family doctor or other unique identifier. At 208, the server computing device 102, in response to receipt of the invitation indication, constructs an invitation and directs the invitation to the e-mail address of the family doctor (such that it is received by the family doctor at the client computing device 118 when the family doctor logs into his or her e-mail account). At 210, the computing device 118 outputs an indication that the family doctor has accepted the invitation, and the acceptance is received at the server computing device 102.

Responsive to receipt of the acceptance, the server computing device 102, at 212, transmits a confirmation that is received at the client computing device 112 (when the patient 122 is operating the client computing device 112). At 214, the participant 126 operates the client computing device 118 to update the care plan of the patient 122. More specifically, data is transmitted from the client computing device 118 to the server computing device 108, wherein the data includes an update to the care plan of the patient 122. As noted above, the update to the care plan of the patient 122 can include test results, observations, etc., in accordance with the role of the participant 126 in the care plan.

At 216, the patient 122 operates the computing device 112 such that a request for care plan information is transmitted to the server computing device 102 (which executes the care plan application 132). In response to receipt of this request, the server computing device causes care plan information (including the update set forth by the participant 126) to be transmitted to the client computing device 112 at 218. In other words, the patient 122 can log into the care plan application 132, and the care plan application 132 can cause care plan information to be transmitted to the computing device 112 for consumption by the patient 122. This care plan information can include the update provided to the server computing device 102 at 214.

Subsequently, the patient 122 may wish to invite the wellness coach to become a participant in the care plan. Accordingly, at 220, request is transmitted from the client computing device 112 to the server computing device 102, wherein the request indicates that an invitation is to be sent to the wellness coach. Responsive to receipt of this request, at 222, an invitation is constructed by the server computing device 102 and eventually transmitted to the client computing device 110 when operated by the wellness coach. While shown as being a direct connection between the server computing device 102 and the client computing device 110, it is to be understood that there may be several intermediate devices therebetween. At 224, in response to the wellness coach accepting the invitation, the client computing device 110 transmits an indication to the server computing device 102 that the wellness coach has accepted the invitation and is now a participant in the care plan. At 226, the server computing device 102 transmits a confirmation to the computing device 112, thereby informing the patient 122 that the wellness coach has become a participant in the care plan. At 228, the server computing device 102 transmits an update to the computing device 110 indicating that the wellness coach has become a participant in the care plan.

Subsequently, at 230, the wellness coach can operate the client computing device 110 to update the care plan with observations made about the patient 122 by the wellness coach. The server computing device 102 receives the update and updates the care plan of the patient 122. Sometime thereafter, at 232, the participant 126 (the family doctor) operates the client computing device 118 to query the server computing device 102 for care plan information about the patient 122. At 234, in response to receipt of such query, the server device 102 identifies care plan information about the patient 112, including the update set forth by the wellness coach, and causes the care plan information to be provided to the client computing device 118 operated by the family doctor.

The control flow diagram 200 is set forth to illustrate that different participants in a care plan for a patient can be provided with information generated by other participants in the care plan without requiring direct electronic communication between such participants, and further without burdening the patient with entering and communication care plan information amongst and between care providers who are invested in the health of the patient.

Now referring to FIG. 3, an exemplary graphical user interface 300 that can be displayed on a display of a participant (e.g. a display of the client computing device 120 operated by the participant 128) with respect to the patient 122 is illustrated. The graphical user interface 300 includes data that identifies the patient 122. For instance, the graphical user interface 300 can include an image 302 of the patient. Further, the graphical user interface 300 can comprise a field 304 that depicts information about the patient 122, such as a name of the patient 122, a gender of the patient 122, a date of birth of the patient 122 (and/or an age of the patient 122), an identity of an insurance provider that is to be billed for services performed with respect to the patient 122 by the participant 128, etc. The graphical user interface 300 may also include a field 306 the depicts further information pertaining to the patient 122, such as a home address of the patient 122, a telephone number of the patient 122, an e-mail address of the patient 122, a race of the patient 122, and/or an ethnicity of the patient 122.

The graphical user interface 300 also includes a field 308 that depicts identities of the participants in the care plan of the patient 122, as well as respective roles of these participants. For instance, as shown in FIG. 3, the field 308 includes six windows, with each window in the six windows including data about a respective participant in the care plan of the patient 122 and the role of such participant in the care plan of the patient 122. A sixth window 310 in the windows of the field 308 includes graphical indicia that depicts to the participant 128 that the participant 128 is a participant in the care plan of the patient 122. Each of the windows can include a pulldown button that, when selected, causes additional information about the participant corresponding to the window to be presented.

The graphical user interface 300 may also include biographical information about the patient 122 (e.g., as provided by the patient 122). This biographical information can assist participants in the care plan with providing appropriate care to the patient.

The graphical user interface 300 may also include a plurality of selectable tabs 312-318. Selection of the first tab 312 causes goals in the care plan for the patient 122 to be presented. Selection of the second tab 314 causes problems and conditions identified by the patient 122 and/or one or more of the participants in the care plan of the patient 122 to be presented. Selection of the third tab 316 (as shown) causes measures and observations made by participants in the care plan to be presented. Selection of the fourth tab 318 causes data that identifies current prescriptions for the patient 122 to be presented.

Now referring to FIG. 4, another exemplary graphical user interface 400 that can be presented on the client computing device 120 is illustrated. In this exemplary graphical user interface 400, the participant 128 has selected the third tab 316. The graphical user interface 400 includes a plurality of graphical items that are representative of a plurality of health attributes being monitored and/or reported by one or more of the participants in the care plan of the patient 122. In the exemplary care plan that corresponds to the graphical user interface 400, the graphical items represent four different health attributes: 1) blood sugar; 2) 3-month blood sugar average; 3) thyroid producing hormones; and 4) cholesterol levels. A health attribute represented in the graphical user interface 400 may have several sub-attributes. For instance, the health attribute "cholesterol levels" has three different sub-attributes for which measures and/or observations may be entered: HDL, LDL, and triglycerides.

Furthermore, each graphical item that represents a health attribute can include a checkbox that allows the participant 128 to define which health attributes the participant 128 wishes to monitor. In FIG. 4, all of the checkboxes are checked; thus, the participant 128 in the care plan of the patient 122 is subscribing to the health attributes mentioned above. Each graphical item can include: 1) data that identifies a most recent measure for the health attribute represented by the graphical item; 2) an identity of the participant in the care plan who reported the measure; and 3) when the next measure for the health attribute (or sub-attribute) is due. For instance, with respect to the health attribute "blood sugar", the patient 122 last reported her blood sugar at a particular time. Further, data is provided that indicates when the next measure is to be reported (every day before and after meals and at bedtime), as well as identities of participants in the care plan of the patient 122 that are monitoring the health attribute.

In the example shown in FIG. 4, features pertaining to the health attribute "blood sugar" include a selectable button 402, that, when selected by the participant 128, allow the participant 128 to report a measure about health attribute. The graphical item representing the health attribute "blood sugar" (and graphical items representing other health attributes) may also include a button 404 that, when selected, causes historic measures reported for the health attribute corresponding to the button 404 to be displayed. Still further, the data displayed for the health attribute may also include data that identifies the test that is to be performed to obtain measures and/or observations about the health attribute.

Thus, the participant 128, when reviewing the data shown when the third tab 316 is selected, can be provided with graphical items corresponding to health attributes and/ or sub-health attributes. For each health attribute, the following information can be presented: 1) a measure or observation most recently set forth for the health attribute; 2) an identity of the participant in the care plan of the patient 122 that set forth the measurement or observation; 3) data that identifies when the next measurement or observation about the health attribute is scheduled to be reported; 4) data that identifies the participant (or participants) in the care plan who is monitoring the health attribute; 5) a button that allows a measurement or observation about the health attribute to be reported; and 6) a button that allows for historic measurements or observations about the health attribute to be presented. Further, if a measurement or observation about a health attribute is overdue, a graphical icon can be presented that indicates to the participant in the care plan of the patient 122 that a measurement or observation is overdue for the health attribute. In the example shown in FIG. 4, a measurement or observation about a 3-month blood sugar average, as well as a measurement or observation about thyroid producing hormones, is overdue.

Now referring to FIG. 5, an exemplary graphical user interface 500 that can be presented responsive to a participant in the care plan of the patient selecting a pulldown button about a participant in the care plan of the patient is illustrated. In this exemplary graphical user interface 500, the participant that is logged into the care plan application 132 has selected pulldown menu corresponding to his or her own name (Dr. Jerry Atchins, MD). This provides the participant 128, for example, with information indicative of the participant's role in the care plan for the patient 122. For instance, the graphical user interface 500 includes a first field 502 that comprises an image 504 of the participant 128, a name of the participant 128, and an identity of the role of the participant 128 with respect to the patient 122 (e.g., the endocrinologist of the patient 122). The field 502 can also include historical information about the participant 128 with respect to the patient 112. In the example shown in FIG. 5, the participant 128 has been providing care for the patient 122 for over six years, the participant 128 last saw the patient 122 approximately 3 months ago, and the participant 128 joined the care plan for the patient 122 approximately 2 years ago. The field 502 may also include data that indicates when the patient 122 is next scheduled to meet with the participant 128.

The graphical user interface 500 also includes a field 506 that includes data indicative of health attributes of the patient 122 being monitored by the participant 128. The field 506 can include several buttons 508 and 510, wherein the button 508 is a view button that, when selected by the participant 126, causes a graphical user interface to be presented that includes additional information about the health attributes being monitored by the participant 128. The button 510, when selected, causes a graphical user interface to be presented to the participant 128 that allows the participant to alter health attributes being monitored by the participant 128.

The graphical user interface 500 also includes a field 512 that includes data that identifies what information about the patient 122 the participant 128 is subscribing to in the care plan. In this example, the care plan includes three problems for the patient 122, and the participant 128 is subscribing to information about all of such problems. In another example, the field 512 indicates that the patient 122 has two goals in the care plan, and the participant 128 is subscribing to information about such goals.

The graphical user interface 500 also includes a field 514 that depicts what data the participant 128 in the care plan of the patient 122 is tasked with reporting. For instance, as shown in FIG. 5, the participant 128 is scheduled to report results for HbA1c, results for TSH, and results for HDL, LDL and triglycerides. The graphical user interface 500 additionally comprises a field 516 that depicts which prescriptions are being managed by the participant 128. A field 518 illustrates information that has been previously published in the care plan of the patient 122 by the participant 128. Finally, the graphical user interface 500 includes a field 520 that includes contact information of the participant 128, including a name of an enterprise where the participant 128 is employed, an address of such enterprise, a telephone number, a fax number, a web page etc.

Figure 6:
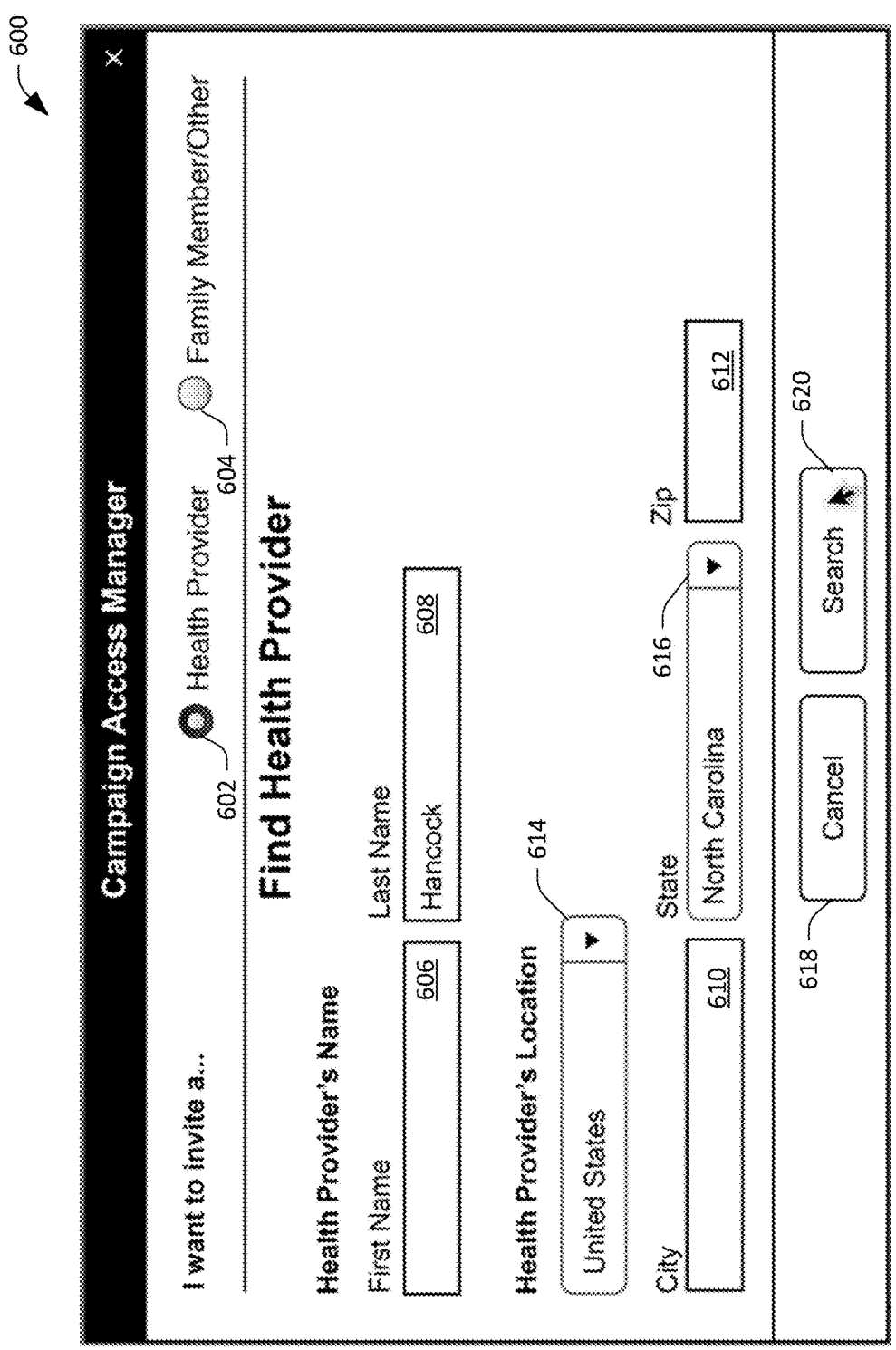
FIG. 6 illustrates an exemplary graphical user interface that facilitates identifying a clinician to add as a care provider in a care plan of a patient.

Now referring to FIG. 6, an exemplary graphical user interface 600 that is well-suited to assist in constructing an invitation to participate in a care plan of the patient 122 is illustrated. The graphical user interface 600 includes radio buttons 602 and 604 that indicate whether or not the individual to be invited to participate in the care plan of the patient 122 is a health provider or a family member (or other). In the example shown in FIG. 6, the participant 128 has selected the health provider radio button 602. The graphical user interface further includes several text entry fields 604-612, as well as pulldown fields 614 and 616. In the text entry field 606 and 608, the participant 128 can enter a first name and/or last name, respectively, of a healthcare provider that is to be invited to participate in the care plan of the patient 122. The pulldown 614 facilitates identification of a country where the healthcare provider is located. The participant 128 may then set forth a name of a city where the healthcare provider practices in the text entry field 610, and may set forth a ZIP code of the location where the healthcare provider practices in the text entry field 612. The pulldown 616 can be employed to select a state or other sub-region of the selected country set forth by way of the pulldown 614.

From reviewing FIG. 6, it can be ascertained that the participant 128 need not enter text into each of the text entry fields 606-612, nor does the participant 128 need to select all locations by way of the pulldown 614 and 616. Instead, in this example, the participant 128 has identified only the last name of the healthcare provider that is to be invited, as well as information indicating that such healthcare provider practices in the state of North Carolina. The graphical user interface 600 further includes a cancel button 618 and a search button 620. Selection of the cancel button 618 may cause the text entry fields and/or pulldowns to be reset to default values, or may cause the graphical user interface 602 be closed. Selection of the button 620 causes a search to be performed based upon the data set forth in the text entry fields 606-612 and/or pulldowns 614 and 616.

Now referring to FIG. 7, another exemplary graphical user interface 700 is depicted. In the graphical user interface 700, a field 702 is provided that includes results of the search performed by way of the graphical user interface 600. In the example shown in FIG. 7, one search result has been returned, although it is to be understood that, for some searches, multiple search results may be returned. The search results can include an identity of the healthcare provider, an identity of the enterprise for which the healthcare provider works, an address of the healthcare provider, and a telephone number of the healthcare provider. The field 702 also includes a button 704 corresponding to a search result, wherein selection of the button 704 causes the corresponding search result (in this case the search result for "John Hancock") to be selected.

With reference now to FIG. 8, an exemplary graphical user interface 800 that can be presented on a display of a computing device operated by a participant in the care plan of the patient 122 who wishes to invite another individual to become a participant in the care plan of the patient 122 is illustrated. In this example, the graphical user interface 800 can be presented on a display of the computing device 112 operated by the patient 122. The graphical user interface 800 includes a field 802 that identifies the individual who is to be invited to participate in the care plan of the patient 122. The graphical user interface 800 also includes radio buttons 804-812. The first radio button 804 identifies how the participant sending the invitation knows the invitee. In this example, the patient 122 indicates that she knows the healthcare provider "John Hancock" because she is a patient of such provider. The graphical user interface 800 also includes options that allow the patient 122 to indicate the last time that the patient 122 was provided care from the healthcare provider "John Hancock", as well as how long the patient has been seeing the health provider "John Hancock".

If the invitor is another participant (heathcare provider) in the care plan of the patient 122, such participant would select the radio button 806, indicating that the invitee is a colleague of "John Hancock". Selection of the radio button 808 can indicate to the invitee that the invitor is neither a patient of the invitee nor a colleague of the invitee. Instead, for instance, the invitor may be a legal representative of the patient 122. The radio buttons 810 and 812 describe permissions that will be provided for the invitee with respect to the care plan of the patient 122. In this example, the radio button 812 is selected, indicating that "John Hancock" is authorized to view, subscribe, and contribute information to the care plan of the patient 122. The graphical user interface 800 can further include a text entry field 814, where the invitor may set forth a personalized message to the invitee. A cancel button 816, when selected, may cancel the invitation, while a send button 818, when selected, can cause the invitation to be transmitted to the invitee.

Figure 9:
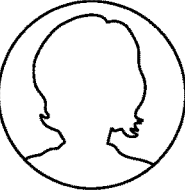
FIG. 9 illustrates a graphical user interface that can be provided to a potential participant in a care plan of a patient.

Now referring to FIG. 9, an exemplary graphical user interface 900 that can be presented on a display of a computing device of the invitee is illustrated. The graphical user interface 900 includes a field 902 with summary information, which identifies who generated the invitation for the invitee (identifies the invitor), and further identifies tasks that the invitee is to perform in the care plan of the patient 122. The graphical user interface 900 can include another field 904 that comprises data that identifies the patient 122 (who, in this example, is the invitor). The field 904 can include, for example, a picture of the patient 122, as well as an indication of when the invitee last provided care to the patient 122. The field 904 may also include data that identifies other participants in the care plan for the patient 122, as well as their respective roles in the care plan of the patient. The graphical user interface 900 also includes buttons 906-910. When the button 906 is selected, an indication is transmitted to the care plan application 132 that the invitee has accepted the invitation. When the invitee selects the button 908, an indication is transmitted to the care plan application 132 that invitation has been declined. When the button 910 is selected, a reminder is provided the invitee at some later time.

Figure 10:
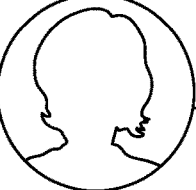
FIG. 10 is a graphical user interface that illustrates that a care provider has been added to a care plan of a patient.

Turning now to FIG. 10, another exemplary graphical user interface 1000 that can be presented on a computing device of an invitee to the care plan of the patient 122 is illustrated. The graphical user interface 1000 is similar to the graphical user interface 900 shown in FIG. 9; however, the field 904 is updated to indicate that the invitee has accepted the invitation and is now amongst the care plan participants (e.g., the graphical user interface 1000 indicates that the healthcare provider "John Hancock" is now a participant in the care plan of the patient 122).

Referring now to FIG. 11, yet another graphical user interface 1100 that may be presented on a computing device operated by a participant in the care plan of the patient 122 is illustrated. The graphical user interface 1100 identifies contributions being made to the care plan of the patient 122 by the participant 128. For instance, the graphical user interface 1100 includes fields for: 1) health goals; 2) problems and conditions; 3) measures and observations; and 4) prescriptions, respectively. The graphical user interface 1100 includes graphical features that allow the participant 128 to readily ascertain the role of the participant 128 in the care plan of the patient 122, as well as roles of other participants in the care plan of the participant 122. Further, the graphical user interface 1100 can provide the participant 128 with a high level perspective of who is performing which task in the care plan of the patient. For instance, five participants are monitoring details pertaining to Type I Diabetes of the patient 122. Further, redundancies can be highlighted. For instance, a graphical highlight can be set forth that indicates to the participant 128 that someone else is also reporting test results for HbA1C, indicating a possible duplication of services.

Figure 12:
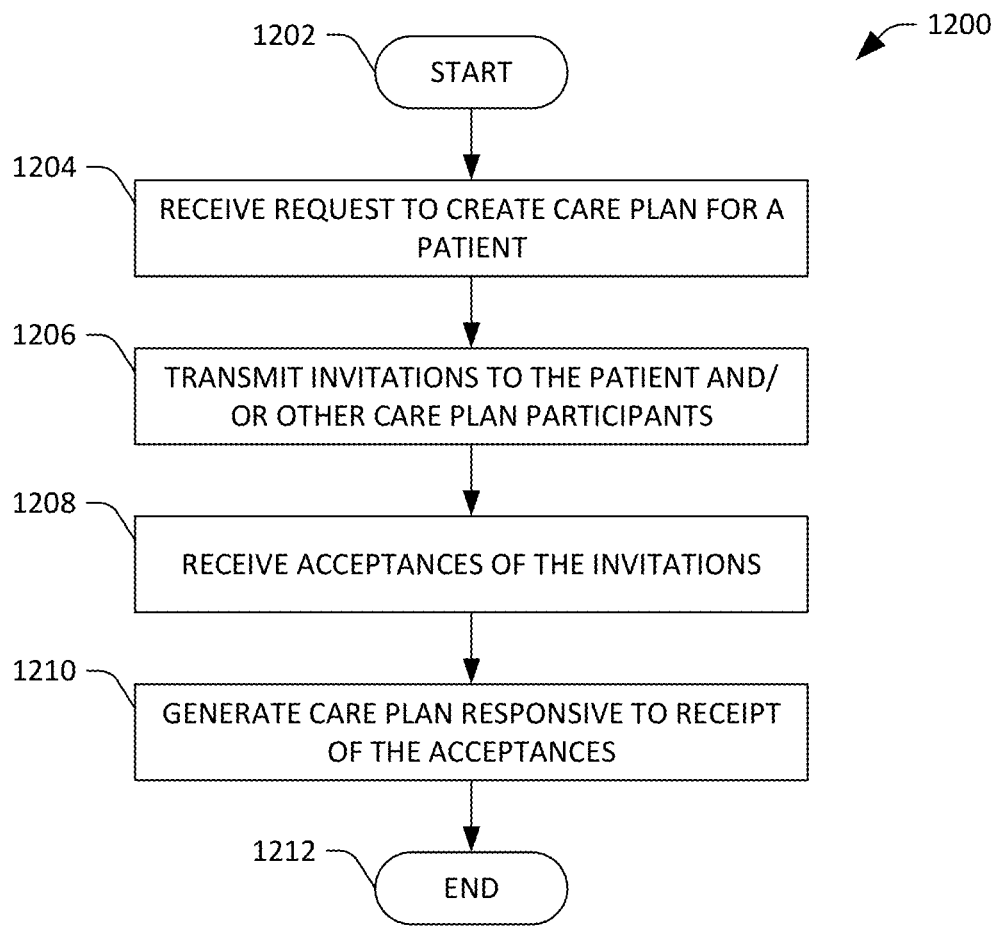
FIG. 12 is a flow diagram that illustrates an exemplary methodology for generating an electronic care plan for a patient.
Figure 13:
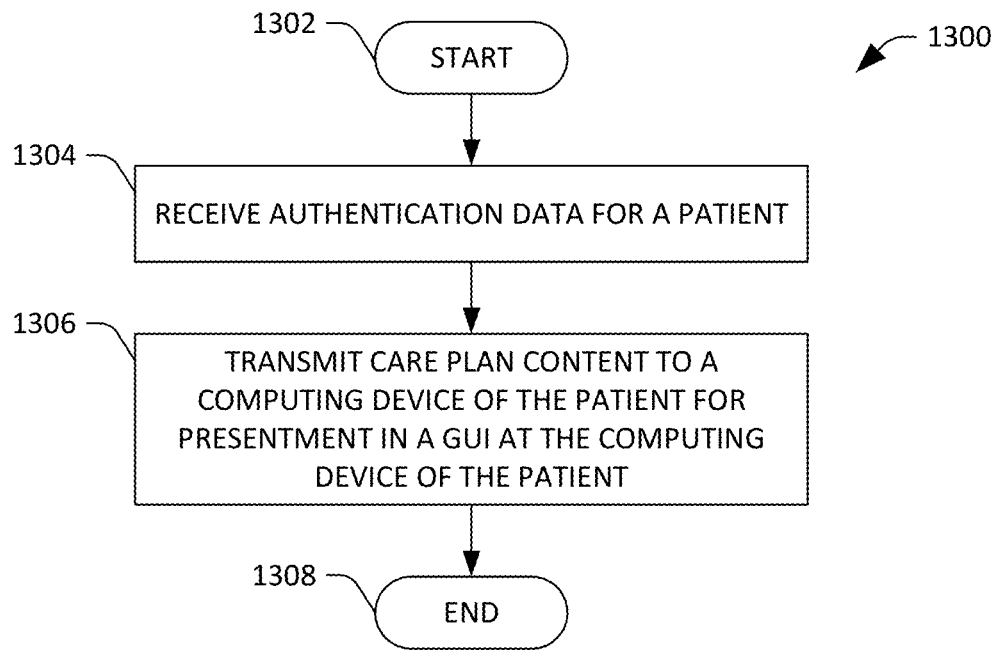
FIG. 13 is a flow diagram that illustrates an exemplary methodology for transmitting care plan content to a computing device operated by a patient.
Figure 14:
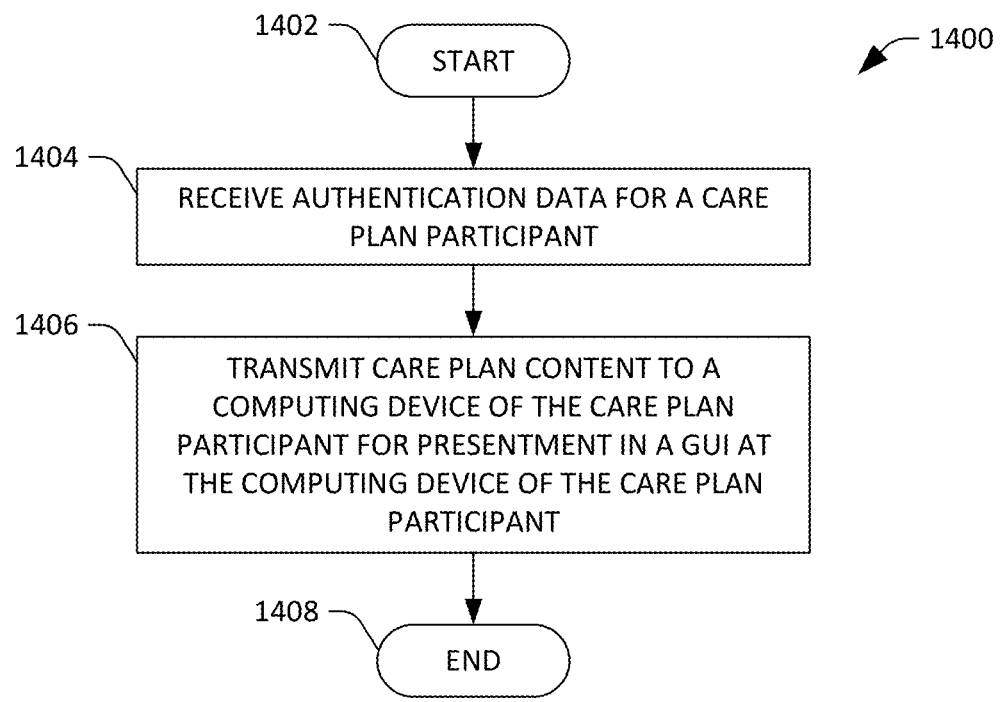
FIG. 14 is a flow diagram that illustrates an exemplary methodology for transmitting care plan content to a computing device operated by a participant in a care plan.

FIGS. 12-14 illustrate exemplary methodologies relating to computing operations that are performed with respect to a care plan of a patient. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

With reference now solely to FIG. 12, an exemplary methodology 1200 (which can be executed at the server computing device 102) is illustrated. The methodology 1200 starts at 1202, and at 1204 a request to create an electronic care plan for a patient is received. For instance, this request can be received from a computing device operated by the patient or a computing device operated by a care provider for the patient. At 1206, invitations to the patient and/or those identified as being desired care plan participants can be generated and transmitted. For example, the creator of the care plan can identify who else should be a participant in the care plan. At 1208, acceptances of the invitations are received from computing devices operated by invited individuals. At 1210, the electronic care plan is generated responsive to receipt of the acceptances. As indicated previously, the invitations sent to the prospective participants in the care plan can define roles of such participant in the care plan. The methodology 1200 completes at 1212.

Now referring to FIG. 13, another exemplary methodology 1300 is illustrated, wherein the methodology 1300 can be executed at the server computing device 102. The methodology 1300 starts at 1302, and at 1304 authentication data for a patient is received. For example, the patient can set forth a user name, password, or other identifying indicia to the server computing device 102, and the care plan application 132 can authenticate the patient based upon this data. At 1306, care plan content is transmitted to a computing device of the patient for presentment in a graphical user interface at the computing device of the patient. This graphical user interface may be presented in a browser, in a mobile application, etc. The methodology 1300 completes at 1308.

Turning now to FIG. 14, another exemplary methodology 1400 that can be executed at the server computing device 102 is illustrated. The methodology 1400 starts at 1402, and at 1404 authentication data is received for a care plan participant (a care provider). This authentication data can include an identity of a patient, as well as authentication data for the care provider (e.g. username and password for the care provider or other identifying indicia). The care plan application 132 can authenticate the care provider based upon such authentication data.

At 1406, care plan content is transmitted to a computing device of the care plan participant for presentment in a graphical user interface at the computing device of the care plan participant. The care plan content may include, for instance, data that identifies the patient, data that identifies the care plan participant, data that identifies other participants in the care plan, data that identifies the roles of the care plan participants, and so forth. The methodology 1400 completes at 1408.

Figure 15:
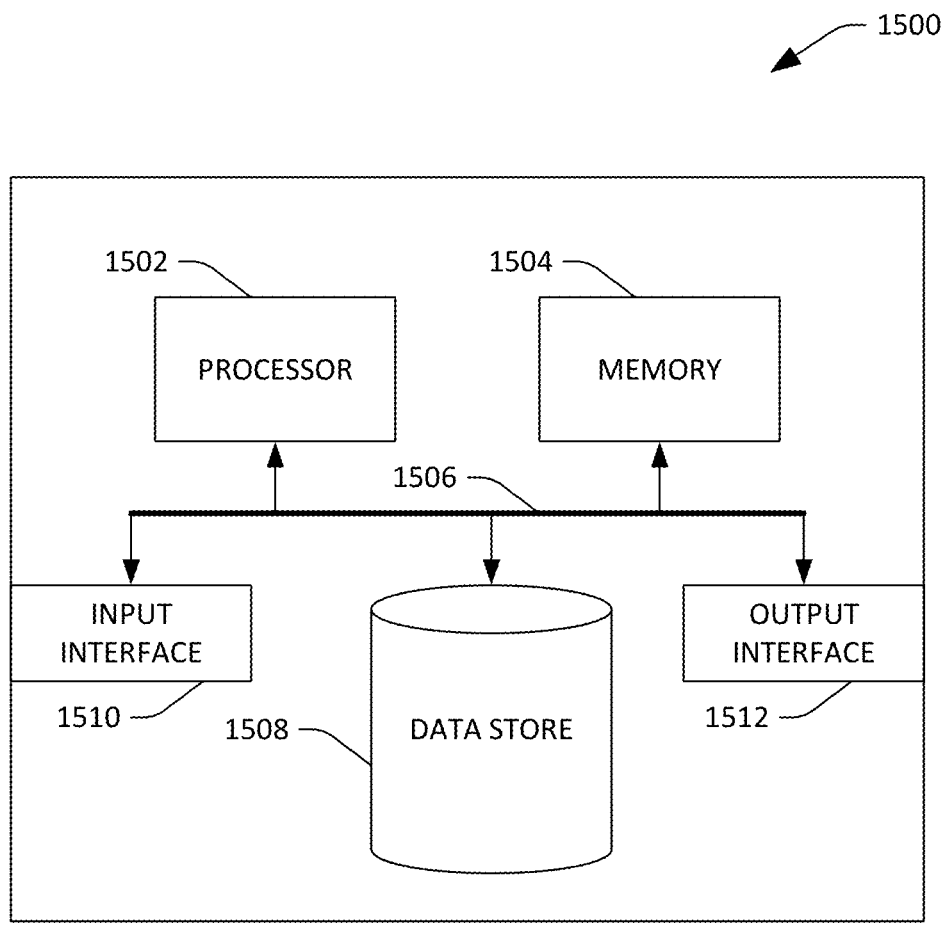
FIG. 15 is an exemplary computing system.

Referring now to FIG. 15, a high-level illustration of an exemplary computing device 1500 that can be used in accordance with the systems and methodologies disclosed herein is illustrated. For instance, the computing device 1500 may be used in a system that is configured to create an electronic care plan for a patient. By way of another example, the computing device 1500 can be used in a system that is configured to cause graphical user interfaces pertaining to a care plan of a patient to be presented on a display of a computing device. The computing device 1500 includes at least one processor 1502 that executes instructions that are stored in a memory 1504. The instructions may be, for instance, instructions for implementing functionality described as being carried out by one or more components discussed above or instructions for implementing one or more of the methods described above. The processor 1502 may access the memory 1504 by way of a system bus 1506. In addition to storing executable instructions, the memory 1504 may also store care plan parameters, such as identities of participants in a care plan, goals for a patient set forth in the care plan, etc.

The computing device 1500 additionally includes a data store 1508 that is accessible by the processor 1502 by way of the system bus 1506. The data store 1508 may include executable instructions, care plan parameters, etc. The computing device 1500 also includes an input interface 1510 that allows external devices to communicate with the computing device 1500. For instance, the input interface 1510 may be used to receive instructions from an external computer device, from a user, etc. The computing device 1500 also includes an output interface 1512 that interfaces the computing device 1500 with one or more external devices. For example, the computing device 1500 may display text, images, etc. by way of the output interface 1512.

It is contemplated that the external devices that communicate with the computing device 1500 via the input interface 1510 and the output interface 1512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1500 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1500 may be a distributed system. Thus, for instance, several devices may be in communication by way of a network connection and may collectively perform tasks described as being performed by the computing device 1500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device comprising:
   at least one processor;
   computer-readable storage comprising computer-readable data, wherein the computer-readable data stored in the computer-readable storage is constructed based upon data received from a first electronic health record application (EHR) executing on a first computing device and a second EHR executing on a second computing device, wherein the first EHR and the second EHR are not configured to communicate with each other, and further wherein the computer-readable data comprises:
   an identity of each participant amongst multiple participants in a care plan of a patient, wherein the patient is a participant in the multiple participants, and further wherein the care plan identifies multiple health attributes of the patient that are to be monitored by the multiple participants; and
   a role of each participant in the multiple participants in the care plan of the patient, the role of each participant identifies which of the health attributes is to be monitored by each participant in the multiple participants;

memory that has a care plan application loaded therein that, when executed by the at least one processor, causes the at least one processor to perform acts comprising:

receiving a request from a client computing device operated by the patient to access the care plan;

in response to receipt of the request from the client computing device operated by the patient, causing a graphical user interface (GUI) to be presented on a display of the client computing device based upon the computer-readable data, wherein the GUI comprises:

a first field comprising the identity of each participant in the multiple participants in the care plan of the patient, wherein the first field further comprises the role of each participant in the multiple participants in the care plan of the patient;

a second field configured to receive input comprising information pertaining to a potential participant of the care plan; and a plurality of selectable tabs pertaining to different subsections of the care plan; and in response to receipt of contact information for the potential participant from the client computing device, transmitting an invitation to a second client computing device of the potential participant based upon the contact information for the potential participant, wherein the client computing device received the contact information for the potential participant by way of the second field of the GUI, and further wherein the invitation invites the potential participant to participate in the care plan for the patient.

2. The server computing device of claim 1, wherein the multiple participants in the care plan of the patient operate different computing devices in network communication with the server computing device.

3. The server computing device of claim 1, the acts further comprising:

prior to causing the GUI to be presented on the display of the client computing device, receiving results of a test performed with respect to the patient, the results of the test generated based upon interaction of a care provider who is a participant in the care plan with a third client computing device operated by the care provider, wherein the GUI further comprises the results of the test.

4. The server computing device of claim 3, wherein the results of the test comprise data that identifies the care provider under whose observation the test was performed.

5. The server computing device of claim 1, the computer-readable data further comprising:

an identity of a medication prescribed to the patient by a care provider included in the multiple participants;

an identity of a diagnosis of the patient that is to be monitored by the care provider, wherein the acts further comprise:

in response to receipt of a second request received from a third client computing device operated by the care provider, causing a second GUI to be presented on a second display of the third client computing device, wherein the second GUI comprises:

a third field comprising an identifier pertaining to the patient;

a fourth field comprising the identity of the medication prescribed to the patient by the care provider;

a fifth field comprising the identity of the diagnosis of the patient that is to be monitored by the care provider; and a sixth field comprising an identity of a second care provider included in the participant in the care plan of the patient.

6. The server computing device of claim 1, wherein at least a portion of the computer-readable data is received from a second server computing device that executes a third EHR, wherein the third EHR is configured to cause the second server computing device to transmit the portion of the computer-readable data to the server computing device.

7. The server computing device of claim 1, wherein at least a portion of the computer-readable data is retrieved from a second server computing device that executes a health information exchange (HIE) that interfaces with a server EHR, wherein the server computing device is configured to retrieve the portion of the computer-readable data from the second server computing device.

8. The server computing device of claim 1, wherein at least a portion of the computer-readable data is received from a second server computing device that executes a patient portal application, the patient portal application configured to present health data to the patient and receive health data from the patient.

9. The server computing device of claim 1, the acts further comprising:

receiving, from the first computing device, an identity of a clinician that is to be added as a participant to the care plan of the patient;

responsive to receiving the identity of the clinician, transmitting an invitation to a third client computing device that is operated by the clinician, the invitation inviting the clinician to be added as a participant to the care plan of the patient; and responsive to receiving an indication that the clinician has accepted the invitation, updating the computer-readable data in the computer-readable storage to indicate that the clinician has been added as a participant to the care plan and to further indicate a role of the clinician in the care plan.

10. The server computing device of claim 1, the acts further comprising:

receiving, from a third client computing device operated by a participant included in the plurality of participants in the care plan of the patient, an identity of a clinician that is to be added as an additional participant to the care plan of the patient;

responsive to receiving the identity of the clinician, transmitting an invitation to a fourth client computing device that is operated by the clinician, the invitation inviting the clinician to be added as a participant to the care plan of the patient; and responsive to receiving an indication that the clinician has accepted the invitation, updating the computer-readable data in the computer-readable storage to indicate that the clinician has been added as a participant to the care plan and to further indicate a role of the clinician in the care plan.

11. A method executed at a server computing device that is in network communication with a plurality of computing devices, the method comprising:

receiving, at the server computing device from a care plan application, authentication data for a patient, the patient has a care plan assigned thereto;

in response to receiving the authentication data, causing a first graphical user interface (GUI) to be presented on a display of a first client computing device of the patient, wherein the first GUI presents data from a first electronic health record application (EHR) executing on a first server computing device and a second EHR executing on a second server computing device, wherein the first EHR and the second EHR are not configured to communicate with each other, and further wherein the first GUI comprises:
  a first field comprising identities of a plurality of participants in the care plan assigned to the patient, wherein at-a first participant in the plurality of participants is associated with a first healthcare enterprise and a second participant in the plurality of participants is associated with a second healthcare enterprise;
  a second field comprising contact information for each participant in the plurality of participants;
  a third field comprising a role of each participant in the participants with respect to the care plan of the patient, wherein the role of the participant identifies a health attribute of the patient that the participant is to monitor over a duration of the care plan;
  a fourth field configured to receive input comprising information pertaining to a potential participant of the care plan; and
  a plurality of selectable tabs pertaining to different subsections of the care plan; and
transmitting an electronic invitation to a second client computing device that is operated by the potential participant in response to receipt of contact information for the potential participant from the first client computing device, wherein the contact information for the potential participant is received by way of the fourth field of the GUI shown on the first client computing device, and further wherein the invitation invites the potential participant to be added to the care plan for the patient.

12. The method of claim 11, wherein the potential participant is a clinician, the invitation identifies a role of the clinician in the care plan;
  receiving, by way of the second client computing device of the clinician, an acceptance to the invitation; and
  responsive to receiving the acceptance to the invitation, updating the first GUI to include an identity of the clinician in the first field, contact information for the clinician in the second field, and the role of the clinician in the care plan in the third field.

13. The method of claim 12, wherein the invitation is transmitted to the second client computing device of the clinician by way of the second server computing device that executes the second EHR, the second EHR transmits the invitation to the second client computing device of the clinician.

14. The method of claim 13, further comprising:
  prior to receiving the authentication data for the patient, transmitting a second invitation to a third client computing device of a second clinician, the second invitation inviting the second clinician to participate in the care plan of the patient, the second invitation identifies a role of the second clinician in the care plan;
  receiving, by way of the third client computing device of the second clinician, an acceptance to the second invitation; and
  responsive to receiving the acceptance to the second invitation, updating the first GUI with an identity of the second clinician in the first field, contact information for the second clinician in the second field, and the role of the second clinician in the care plan in the third field.

15. The method of claim 14, wherein the invitation is transmitted to the third client computing device of the second clinician by way of the second server computing device, the second EHR transmits the invitation to the third client computing device of the second clinician.

16. The method of claim 11, further comprising:
  receiving second authentication data for a participant included in the plurality of participants in the care plan by way of a client computing device of the participant;
  responsive to receiving the second authentication data, causing a second GUI to be presented on a display of the client computing device of the participant, the second GUI comprises:
    a fifth field comprising diagnoses of the patient to be monitored by the participant;
    a sixth field comprising identities of other participants of the care plan of the patient; and
    a seventh field comprising an identity of a medication prescribed to the patient by the participant.

17. The method of claim 16, further comprising:
  receiving, by way of the client computing device of the participant included in the plurality of participants, an invitation to be provided to a client computing device of a clinician, the invitation inviting the clinician to become a participant in the care plan;
  responsive to receiving the invitation, transmitting the invitation to the client computing device of the clinician;
  receiving, by way of the client computing device of the clinician, an acceptance of the invitation; and
  responsive to receiving the acceptance of the invitation, updating the first GUI with an identity of the clinician in the first field, contact information for the clinician in the second field, and the role of the clinician in the care plan in the third field.

18. The method of claim 11, wherein the first GUI further comprises a fifth field comprising test results for the patient, wherein the test results are for a test ordered for the patient by a participant of the care plan, and wherein the first GUI indicates that the test results correspond to the participant of the care plan.

19. The method of claim 11, wherein the first GUI further includes a fifth field comprising goals for the patient in the care plan.

20. A non-transitory computer-readable storage medium comprising instructions that, when executed by a processor, cause the processor to perform acts comprising:
  in response to receipt of authentication data for a patient who has a care plan assigned thereto, retrieving care plan data from the computer-readable storage, wherein the care plan data is constructed based upon data received from a first electronic health record application (EHR) executing on a first computing device and a second EHR executing on a second computing device, wherein the first EHR and the second EHR are not configured to communicate with each other, and further wherein the care plan data comprises data crowd-sourced from a plurality of participants in the care plan and the patient, wherein a first participant in the plurality of participants in the care plan is an employee at a first healthcare enterprise, a second participant in the plurality of participants is an employee at a second healthcare enterprise, and further wherein each participant in the care plan is assigned a role in the care plan of the patient;

responsive to retrieving the care plan data from the computer-readable storage, transmitting the care plan data to a client computing device of the patient for presentment in a graphical user interface (GUI) on a display of the client computing device, wherein the care plan data comprises:
    for each participant in the plurality of participants in the care plan, an identity of the participant, wherein the identity of the participant is displayed in a first field of the GUI;
    for each participant in the plurality of participants in the care plan, a role of the participant in the care plan, wherein the role of the participant is displayed in a second field of the GUI; and
    for each participant in the plurality of participants in the care plan, a health attribute of the patient that is being monitored by the participant, wherein the health attribute of the patient is displayed in a third field of the GUI, and further wherein the GUI comprises a field that is configured to receive contact information of a potential participant in the care plan; and
transmitting, to a computing device of the potential participant in the care plan, an invitation upon receiving the contact information of the potential participant by way of the field of the GUI, wherein the invitation invites the potential participant to join the care plan of the patient.

* * * * *